United States Patent
Lee et al.

(10) Patent No.: US 10,867,872 B2
(45) Date of Patent: Dec. 15, 2020

(54) METHOD AND APPARATUS FOR MANUFACTURING SEMICONDUCTOR STRUCTURE

(71) Applicant: TAIWAN SEMICONDUCTOR MANUFACTURING COMPANY LTD., Hsinchu (TW)

(72) Inventors: Yung-Yao Lee, Hsinchu County (TW); Wei-Hsiang Tseng, Hsinchu County (TW)

(73) Assignee: TAIWAN SEMICONDUCTOR MANUFACTURING COMPANY LTD., Hsinchu (TW)

( * ) Notice: Subject to any disclaimer, the term of this patent is extended or adjusted under 35 U.S.C. 154(b) by 0 days.

(21) Appl. No.: 16/397,330

(22) Filed: Apr. 29, 2019

(65) Prior Publication Data

US 2020/0035570 A1 Jan. 30, 2020

Related U.S. Application Data

(60) Provisional application No. 62/711,045, filed on Jul. 27, 2018.

(51) Int. Cl.
*H01L 21/66* (2006.01)
*H01L 21/02* (2006.01)
*G01N 33/00* (2006.01)
*G03F 7/16* (2006.01)

(52) U.S. Cl.
CPC ......... *H01L 22/10* (2013.01); *G01N 33/0031* (2013.01); *G01N 33/0036* (2013.01); *G03F 7/162* (2013.01); *H01L 21/02282* (2013.01)

(58) Field of Classification Search
None
See application file for complete search history.

(56) References Cited

U.S. PATENT DOCUMENTS

| | | | |
|---|---|---|---|
| 6,177,133 B1 * | 1/2001 | Gurer | B05D 1/005 427/240 |
| 6,221,787 B1 * | 4/2001 | Ogata | G03F 7/162 257/E21.259 |
| 6,536,964 B1 * | 3/2003 | Kitano | G03F 7/162 118/52 |
| 8,796,666 B1 | 8/2014 | Huang et al. | |
| 9,012,132 B2 | 4/2015 | Chang | |
| 9,093,530 B2 | 4/2015 | Huang et al. | |
| 9,028,915 B2 | 5/2015 | Chang et al. | |
| 9,146,469 B2 | 9/2015 | Liu et al. | |
| 9,213,234 B2 | 12/2015 | Chang | |
| 9,223,220 B2 | 12/2015 | Chang | |
| 9,256,133 B2 | 2/2016 | Chang | |
| 9,536,759 B2 | 1/2017 | Yang et al. | |
| 9,548,303 B2 | 1/2017 | Lee et al. | |

(Continued)

*Primary Examiner* — Shaun M Campbell
(74) *Attorney, Agent, or Firm* — WPAT, P.C., Intellectual Property Attorneys; Anthony King (57) ABSTRACT

A method for manufacturing a semiconductor structure is provided. The method includes the following operations. A first semiconductor substrate is provided on a spin chuck. A first humidity factor near the first semiconductor substrate is obtained. A resist material is dispensed on the first semiconductor substrate. The spin chuck is rotated at a first speed. The first speed is determined based on the first humidity factor.

20 Claims, 8 Drawing Sheets

(56) References Cited

U.S. PATENT DOCUMENTS

| | | | |
|---|---|---|---|
| 2002/0037462 A1* | 3/2002 | Ogata | H01L 21/67253 430/30 |
| 2005/0175775 A1* | 8/2005 | Shirley | G03F 7/162 427/240 |
| 2013/0137034 A1* | 5/2013 | Fu | G03F 7/16 430/270.1 |

* cited by examiner

FIG. 8

METHOD AND APPARATUS FOR MANUFACTURING SEMICONDUCTOR STRUCTURE

PRIORITY CLAIM AND CROSS-REFERENCE

This application claims the benefit of prior-filed provisional application No. 62/711,045, filed on Jul. 27, 2018.

BACKGROUND

Lithography generally refers to processes for transferring one or more patterns between various media. In lithography, a light-sensitive resist coating is formed over one or more layers to which a pattern is to be transferred. The resist coating is then patterned by exposing it to one or more types of radiation or light that (selectively) passes through an intervening mask containing the pattern. The light causes exposed or unexposed portions of the resist coating to become more or less soluble, depending on the type of resist used (positive or negative). A developer is then used to remove the more soluble areas, leaving the patterned resist in place. The patterned resist can then serve as a template for the underlying layer or layers, which can be selectively etched (or doped or otherwise treated). Once the underlying layer is treated, the patterned resist is removed, for example by being chemically stripped, thus leaving in place the treated layer having the pattern formed therein.

BRIEF DESCRIPTION OF THE DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Embodiments of the present disclosure are discussed in detail below. It should be appreciated, however, that the present disclosure provides many applicable inventive concepts that can be embodied in a wide variety of specific contexts. The specific embodiments discussed are merely illustrative and do not limit the scope of the disclosure.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The humidity level near the semiconductor substrate may affect the fluidity of the resist material. The thickness of the resist layer formed on the semiconductor substrate with the spin chuck rotating at the base speed may fluctuate because of the humidity variation. In some embodiments of the present disclosure, the rotation speed may be modified according to the humidity factor. Thus, the rotation speed may be increased or decreased according to the humidity level near the semiconductor substrate, and the fluctuation in the thickness of the resist layer formed on the semiconductor substrate may be alleviated.

Figure 1:
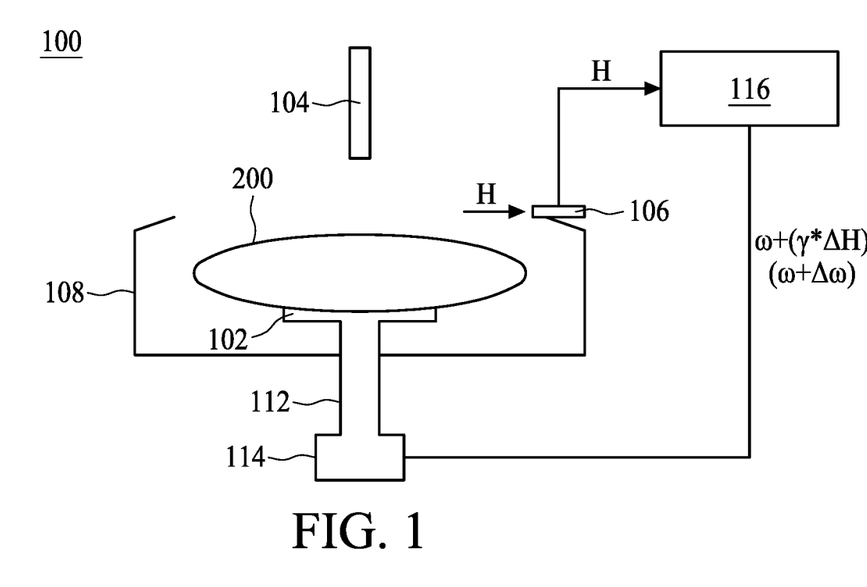
FIG. 1 is a schematic view of an apparatus for manufacturing a semiconductor structure at some stages, in accordance with some embodiments of the present disclosure.
Figure 2:
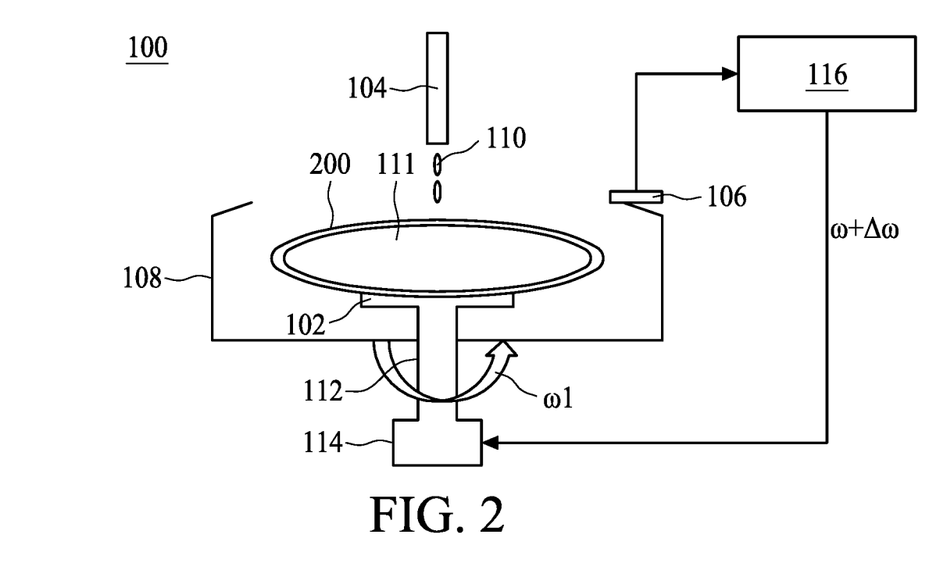
FIG. 2 is a schematic view of an apparatus for manufacturing a semiconductor structure at some stages, in accordance with some embodiments of the present disclosure.

FIG. 1 and FIG. 2 are schematic views of an apparatus for manufacturing a semiconductor structure at some stages, in accordance with some embodiments of the present disclosure. The apparatus 100 includes a spin chuck 102, a dispensing unit 104 and a humidity sensor 106. In some embodiments, the apparatus 100 may further include a cup 108 and a controller 116. The cup 108 has a basin with sidewalls. The controller 116 is communicatively coupled to the humidity sensor 106 and the spin chuck 102. The controller 116 may include a central processing unit (CPU) or other components in a computing module.

The spin chuck 102 is configured to support a semiconductor substrate 200. The spin chuck 102 is a rotatable platform situated inside the cup 108. The spin chuck 102 may be a vacuum chuck, with vacuum applied from the platform for holding the semiconductor substrate 200. During the manufacturing operations, the bottom surface of the semiconductor substrate 200 contacts the spin chuck 102. A suitable vacuum is then applied to the bottom surface of the semiconductor substrate 200 such that the semiconductor substrate 200 is held securely on the spin chuck 102 even at high rotation speeds. The rotating motion of the spin chuck 102 is achieved by a shaft 112, which is connected to the spin chuck 102 and powered by a motor 114.

The dispensing unit 104 is situated over the spin chuck 102 for dispensing a resist material 110 onto the semiconductor substrate 200. The resist material 110 with corresponding viscosity is dispensed on top of the semiconductor substrate 200.

The humidity sensor 106 is configured to sense a humidity information H near the semiconductor substrate 200. In some embodiments, the humidity sensor 106 is attached to the cup 108. In some other embodiments, the humidity sensor 106 is disposed around the dispensing unit 104. In some embodiments, a plurality of the humidity sensors 106 can be disposed near the semiconductor substrate 200, attached to the cup 108, and/or disposed at the dispensing unit 104. In some embodiments, the plurality of the humidity sensors 106 can be placed at several locations of the apparatus 100 in order to obtain a humidity value with representative meaning. In other embodiments, the humidity sensor 106 may be attached to other predetermined positions near the semiconductor substrate 200. The attached position of the humidity sensor 106 is not intended to be limiting.

Referring to FIG. 1, in some embodiments, before the resist material 110 (shown in FIG. 2) is dispensed onto the semiconductor substrate 200, the humidity sensor 106 may begin to sense the humidity information H near the semiconductor substrate 200. The humidity information H is related to the humidity level near the semiconductor substrate 200. The humidity sensor 106 outputs the humidity information H to the controller 116. The controller 116 receives and analyzes the humidity information H to obtain a humidity factor ΔH. The humidity factor ΔH may include information such as current measured humidity information H, prior measured humidity information, and/or a difference between the current measured humidity information H and the prior measured humidity information. In some embodiments, the controller 116 determines a first speed ω1 (shown in FIG. 2), wherein the first speed ω1 is expressed by an equation (1).

$$\omega1=\omega+\Delta\omega=\omega+(\gamma*\Delta H) \qquad (1)$$

where ω is a base speed, and γ is a positive constant.

In some embodiments, γ may be related to a material parameter of the resist material 110.

Referring to FIG. 2, when the resist material 110 is dispensed onto the semiconductor substrate 200, the controller 116 drives the motor 114 to rotate the spin chuck 102 at the first speed ω1. In some embodiments, the first speed ω1 equals the sum of the base speed ω and the modification speed Δω (i.e., the product of γ and ΔH as in equation (1)). The modification speed Δω is dependent on the humidity factor ΔH. In some other embodiments, the base speed ω may be a predetermined speed and is determined according to a material parameter (e.g., viscosity). For example, a greater viscosity of the resist material 110 correlates to a greater base speed ω, and a smaller viscosity of the resist material 110 correlates to a lower base speed ω.

In some embodiments, when the humidity factor ΔH is a positive value, the currently-measured humidity level at the location close to the semiconductor substrate 200 is higher than the previously-measured humidity level, the modification speed Δω is a positive value, and the first speed ω1 is accordingly greater than the base speed ω.

In other embodiments, when the humidity factor ΔH is a negative value, the currently-measured humidity level at the location close to the semiconductor substrate 200 is lower than the previously-measured humidity level, the modification speed Δω is a negative value, and the first speed ω1 is accordingly less than the base speed ω.

In one or more embodiments, the spin chuck 102 may initially rotate at the base speed ω, and the controller may subsequently change the rotation speed of the spin chuck 102 to the first speed ω1 according to the humidity factor ΔH.

When the dispensing of the resist material 110 is completed, a resist layer 111 is formed over the semiconductor substrate 200, and the resist layer 111 is subsequently exposed to a light source (not shown) to form a pattern.

The humidity level near the semiconductor substrate 200 may affect the fluidity of the resist material 110. The thickness of the resist layer 111 formed on the semiconductor substrate 200 with the spin chuck 102 rotating at the base speed ω may fluctuate because of variations in humidity. In some embodiments of the present disclosure, the rotation speed (e.g., the first speed ω1) may be modified according to the humidity factor ΔH. Thus, the rotation speed may be increased or decreased according to the humidity level near the semiconductor substrate 200, and the fluctuation in the thickness of the resist layer 111 formed on the semiconductor substrate 200 may be alleviated.

Figure 3A:
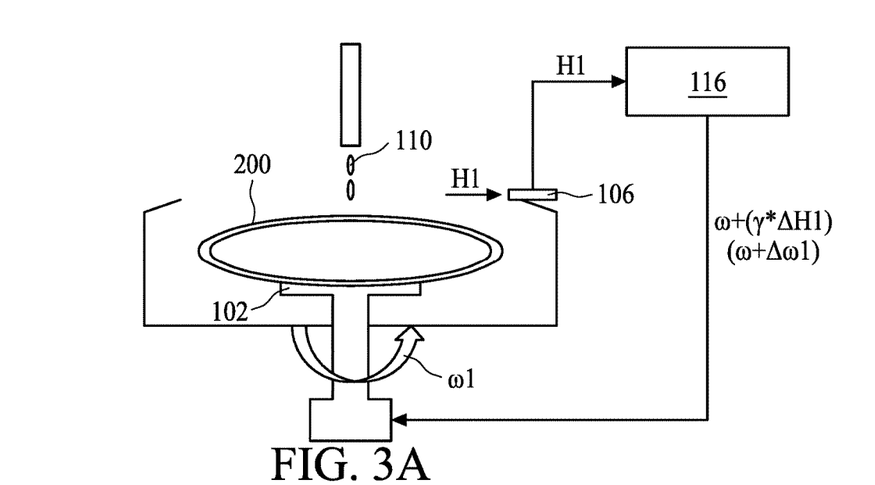
FIG. 3A and FIG. 3B are schematic views of an apparatus for manufacturing a semiconductor structure at some stages, in accordance with some embodiments of the present disclosure.
Figure 3B:
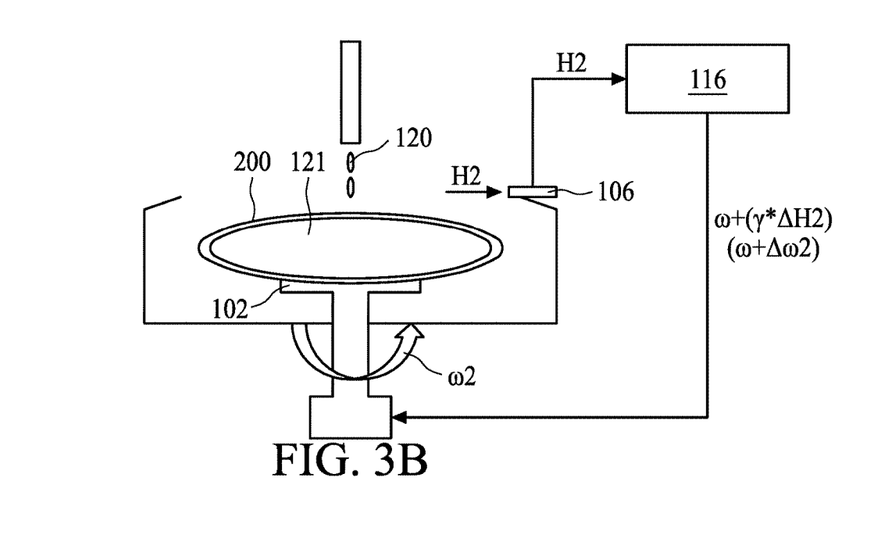

FIG. 3A and FIG. 3B are schematic views of an apparatus for manufacturing a semiconductor structure at some stages, in accordance with some embodiments of the present disclosure. In some embodiments, more than one resist material may be dispensed onto the semiconductor substrate 200. Referring to FIG. 3A, before or during the first resist material 110 is dispensed onto the semiconductor substrate 200, the humidity sensor 106 senses the first humidity information H1. The humidity sensor 106 outputs the first humidity information H1 to the controller 116. The controller 116 receives and analyzes the first humidity information H1 to obtain a first humidity factor ΔH1. The first humidity factor ΔH1 include information such as current measured humidity information, prior measured humidity information, and/or a difference between the current measured first humidity information H1 and the prior measured humidity information. In some embodiments, the controller 116 determines the first speed ω1 wherein the first speed ω1 is expressed by the equation (2).

$$\omega1=\omega+\Delta\omega=\omega+(\gamma*\Delta H1) \qquad (2)$$

Referring to FIG. 3B, when the dispensing of the first resist material 110 is completed, the second resist material 120 may then be dispensed onto the semiconductor substrate 200. Before or during the second resist material 120 is dispensed onto the semiconductor substrate 200, the humidity sensor 106 may sense a second humidity information H2. The humidity sensor 106 outputs the second humidity information H2 to the controller 116. The controller 116 receives and analyzes the second humidity information H2 to obtain a second humidity factor ΔH2. The second humidity factor ΔH2 may include information such as current measured humidity information, prior measured humidity information, and/or a difference between the current measured second humidity information H2 and the prior measured humidity information. In some embodiments, the controller 116 determines the second speed ω2 wherein the second speed ω2 is expressed by the equation (3).

$$\omega2=\omega+\Delta\omega=\omega+(\gamma*\Delta H2) \qquad (3)$$

It should be noted that, depending on the setting, during the determining of the second speed ω2, the base speed ω in equation (3) may use the predetermined speed or the first speed ω1.

For example, if the first speed ω1 is used as the base speed ω in equation (3), the second speed ω2 may be greater than the first speed ω1 when the second humidity factor ΔH2 is a positive value (i.e., the humidity level is increased). The controller 116 may increase the first speed ω1 to the second speed ω2. In other embodiments, the second speed ω2 may be less than the first speed ω1 when the second humidity factor ΔH2 is a negative value (i.e., the humidity level is decreased). The controller 116 may reduce the first speed ω1 to the second speed ω2.

In some embodiments, if the predetermined speed is used as the base speed ω in equation (3), the second speed ω2 may be greater than the predetermined speed and the first speed ω1 when the second humidity factor ΔH2 is a positive value (i.e., the second humidity information H2 is increased from the first humidity information H1. The controller 116 may increase the first speed ω1 to the second speed ω2.

In other embodiments, the second humidity factor ΔH2 may be still a positive value (i.e., the ambient humidity information is used as prior measured humidity information and the second humidity information H2 is increased from the ambient humidity information but lower than the first humidity information H1). The second speed ω2 may be greater than the predetermined speed but lower than the first speed ω1. The controller 116 decreases the first speed ω1 to the second speed ω2.

In other embodiments, the second speed ω2 may be less than the first speed ω1 and the predetermined speed when the second humidity factor ΔH2 is a negative value (i.e., the second humidity information H2 is decreased from the first humidity information H1 or the ambient humidity information). The controller 116 may reduce the first speed ω1 to the second speed ω2.

As described above, the humidity level near the semiconductor substrate 200 may affect the fluidity of the resist materials 110 and 120. The thickness of the resist layers 111 and 121 formed on the semiconductor substrate 200 with the spin chuck 102 rotating at the base speed ω may fluctuate because of variations in humidity. In some embodiments of the present disclosure, the rotation speed may be modified according to the humidity factors ΔH1 and ΔH2. Thus, the rotation speed may be increased or decreased according to the humidity level, and the fluctuation in the thickness of the resist layers 111 and 121 formed on the semiconductor substrate 200 may be alleviated.

Figure 4A:
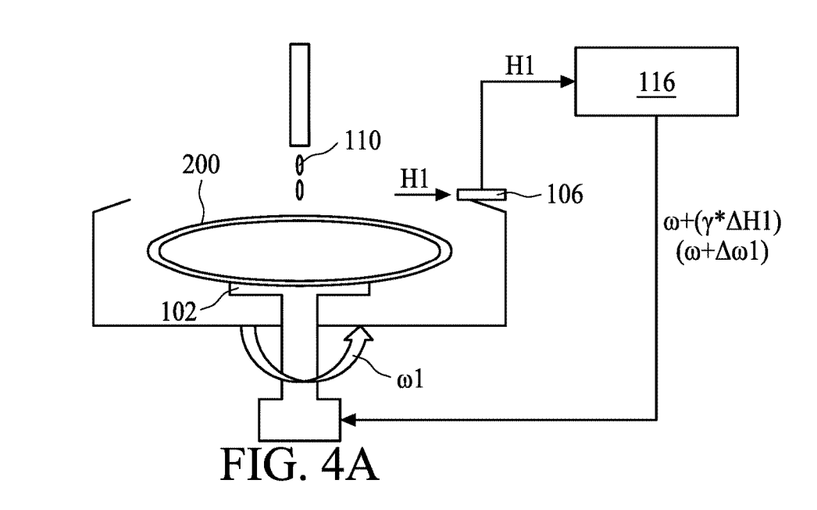
FIG. 4A and FIG. 4B are schematic views of an apparatus for manufacturing a semiconductor structure at some stages, in accordance with some embodiments of the present disclosure.
Figure 4B:
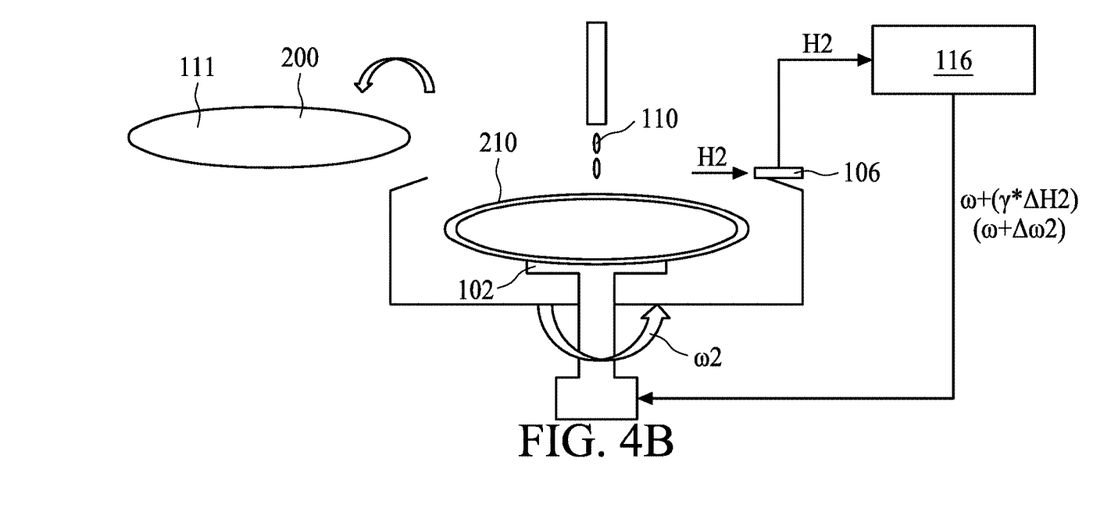

FIG. 4A and FIG. 4B are schematic views of an apparatus for manufacturing a semiconductor structure at some stages, in accordance with some embodiments of the present disclosure. In some embodiments, multiple semiconductor substrates may require the resist material to be dispensed thereon. Referring to FIG. 4A, when the resist material 110 is dispensed onto the first semiconductor substrate 200, the humidity sensor 106 senses the first humidity information H1. The humidity sensor 106 outputs the first humidity information H1 to the controller 116. The controller 116 receives and analyzes the first humidity information H1 to obtain a first humidity factor ΔH1. The first humidity factor ΔH1 may include information such as current measured humidity information H1, prior measured humidity information, and/or a difference between the current measured humidity information H1 and the prior measured humidity information. In some embodiments, the controller 116 determines the first speed ω1 wherein the first speed ω1 is expressed by the equation (2) described above.

Referring to FIG. 4B, when the dispensing of the resist material 110 is finished, the first semiconductor substrate 200 is removed from the spin chuck 102. The second semiconductor substrate 210 is provided to the spin chuck 102 for receiving the resist material 110 to be dispensed thereon. The humidity sensor 106 may sense a second humidity information H2 near the second semiconductor substrate 210. The humidity sensor 106 outputs the second humidity information H2 to the controller 116. The controller 116 receives and analyzes the second humidity information H2 to obtain a second humidity factor ΔH2. The second humidity factor ΔH2 may include information such as current measured humidity information H2, prior measured humidity information, and/or a difference between the current measured humidity information H2 and the prior measured humidity information. In some embodiments, the controller 116 determines the second speed ω2 wherein the second speed ω2 is expressed by the equation (3) mentioned above.

It should be noted that, depending on the setting, during the determining of the second speed ω2, the base speed ω in equation (3) may use the predetermined speed or the first speed ω1.

For example, if the first speed ω1 is used as the base speed ω1 in equation (3), the second speed ω2, may be greater than the first speed ω1 when the second humidity factor ΔH2 is a positive value (i.e., the humidity level is increased). The controller 116 may increase the first speed ω1 to the second speed ω2. In other embodiments, the second speed ω2 may be less than the first speed ω1 when the second humidity factor ΔH2 is a negative value (i.e., the humidity level is decreased). The controller 116 may reduce the first speed ω1 to the second speed ω2.

In some embodiments, if the predetermined speed is used as the base speed ω in equation (3), the second speed ω2 may be greater than the predetermined speed and the first speed ω1 when the second humidity factor ΔH2 is a positive value (i.e., the second humidity information H2 is increased from the first humidity information H1). The controller 116 may increase the first speed ω1 to the second speed ω2.

In other embodiments, the second humidity factor ΔH2 may be still a positive value (i.e., the ambient humidity information is used as prior measured humidity information and the second humidity information H2 is increased from the ambient humidity information but lower than the first humidity information H1). The second speed ω2 may be greater than the predetermined speed but lower than the first speed ω1. The controller 116 decreases the first speed ω1 to the second speed ω1.

In other embodiments, the second speed ω2 may be less than the first speed ω1 and the predetermined speed when the second humidity factor ΔH2 is a negative value (i.e., the second humidity information H2 is decreased from the first humidity information H1 or the ambient humidity information). The controller 116 may reduce the first speed ω1 to the second speed ω2.

It should be noted that the semiconductor substrates 200 and 210 may receive multiple resist materials dispensed thereon, as described in FIG. 3A and FIG. 3B, and the description of the operation is omitted herein for brevity.

As described above, the humidity level near the semiconductor substrates 200 and 210 may affect the fluidity of the resist material 110. The thickness of the resist layer 111 formed on the semiconductor substrates 200 and 210 with the spin chuck 102 rotating at the base speed ω may fluctuate because of variations in humidity. In some embodiments of the present disclosure, the rotation speed may be modified according to the humidity factors ΔH1 and ΔH2. Thus, the rotation speed may be increased or decreased according to the humidity level, and the fluctuation in the thickness of the resist layer formed on the semiconductor substrates 200 and 210 may be alleviated. In some embodiments, a rotating duration at a given rotating speed may be optionally determined based on the given rotating speed, the modification speed Δω, or the humidity level. For example, a rotating duration of the semiconductor substrates 200 at the second speed ω2 may be positively correlated to the second speed ω2, the modification speed Δω (i.e., difference between the second speed ω2 and the first speed ω1), or the second humidity factor ΔH2. In some embodiments, a rotating duration may be increased when a rotation speed of the semiconductor substrates 200 is increase from the first speed ω1 to the second speed ω2. In some embodiments, the rotating duration may be increased when the modification speed Δω is positive. In some embodiments, the rotating duration may be increased when the humidity factor (e.g., ΔH1 or ΔH2) is positive (e.g., the second humidity information shows greater humidity than the first humidity information). In some embodiments, the rotating duration may be increased in response to the positive modification speed Δω or the positive humidity factor while keeping the rotation speed at constant.

In some embodiments, photoresist with an original thickness under a standard humidity level may subsequently turn into a greater thickness when the humidity level increases from the standard humidity level, and similarly, turn into a smaller thickness when the humidity level decreases from the standard humidity level. Therefore, when the humidity level increases, a longer rotating duration and/or a faster rotating speed shall be applied in order to obtain the desired photoresist thickness. In contrast, when the humidity level decreases, a shorter rotating duration and/or a slower rotating speed shall be applied in order to obtain the desired photoresist thickness.

Figure 5:
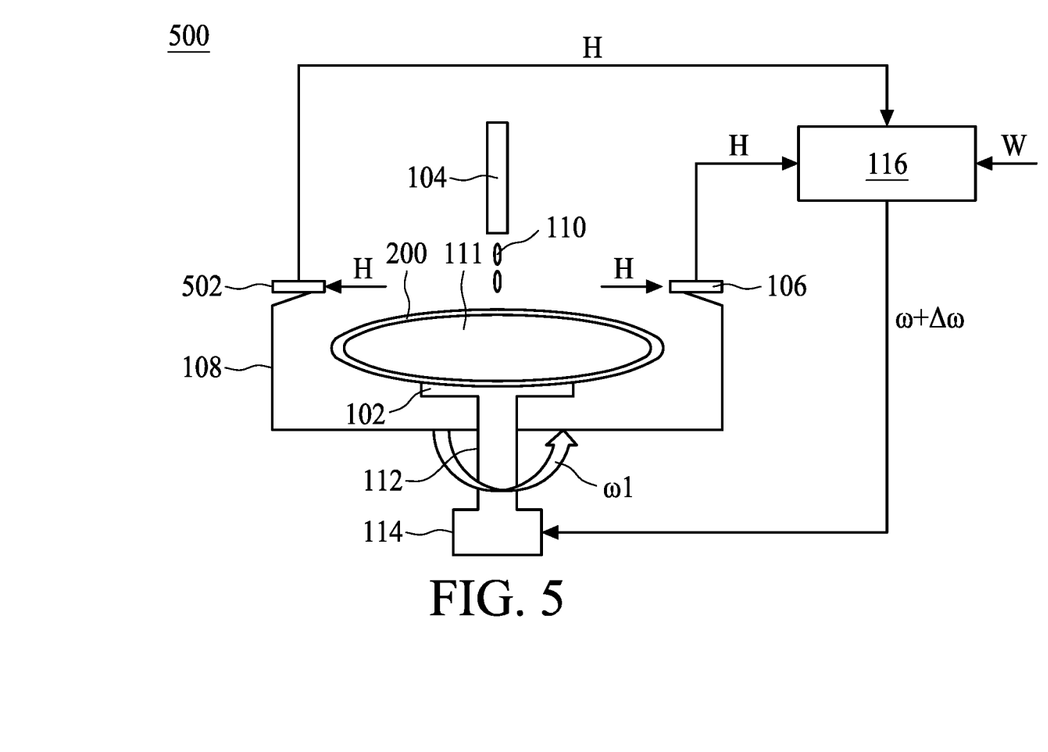
FIG. 5 is a schematic view of an apparatus for manufacturing a semiconductor structure, in accordance with some embodiments of the present disclosure.

FIG. 5 is a schematic view of an apparatus for manufacturing a semiconductor structure, in accordance with some embodiments of the present disclosure. The difference between the apparatus 500 and the apparatus 100 in FIG. 1 is that the apparatus 500 has two humidity sensors 106 and 502. In some embodiments, the humidity sensors 106 and 502 may sense a plurality of humidity information H. The controller 116 analyzes the plurality of humidity information H to determine the humidity factor ΔH. In some embodiments, the controller 116 may obtain an average data of the plurality of humidity information H. The operation of determining the first speed ω1 is similar to the operation described in accordance with FIG. 1 and FIG. 2, and the description of such operation is omitted herein for brevity.

As such, the accuracy of the humidity factor ΔH may be increased, the rotation speed may be precisely controlled, and the fluctuation in the thickness of the resist layer formed on the semiconductor substrate 200 may be alleviated.

Figure 6A:
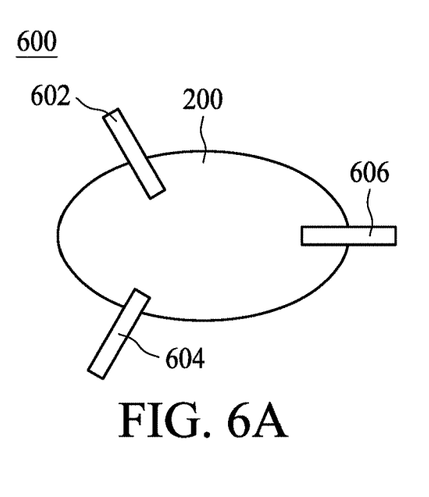
FIG. 6A, FIG. 6B, and FIG. 6C are schematic views of a portion of an apparatus for manufacturing a semiconductor structure, in accordance with some embodiments of the present disclosure.
Figure 6B:
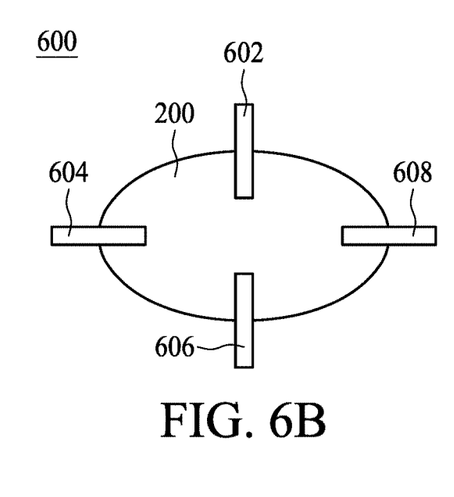
Figure 6C:
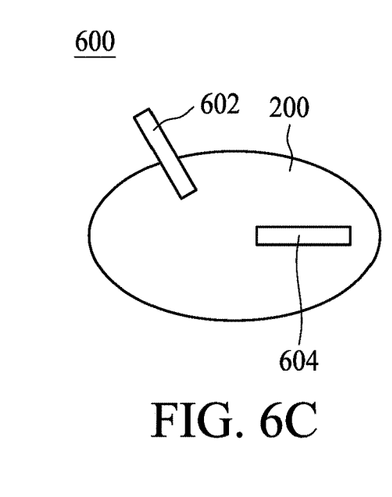

FIG. 6A, FIG. 6B, and FIG. 6C are schematic views of a portion of an apparatus for manufacturing a semiconductor structure, in accordance with some embodiments of the present disclosure. In some embodiments, the apparatus 600 may have more than two humidity sensors. For example, in FIG. 6A, the apparatus 600 may have three humidity sensors 602, 604 and 606, and in FIG. 6B, the apparatus 600 may have four humidity sensors 602, 604, 606 and 608. Of course, the apparatus 600 may have more humidity sensors and the examples provided herein are not intended to be limiting. Moreover, the positions of the humidity sensors are not limited. In some embodiments, the humidity sensors may be disposed over the substrate in an equal-angle fashion. For example, an inclusive angle between any of the two adjacent humidity sensors can be identical. In some embodiments, the apparatus 600 may have one or more humidity sensors configured to obtain a humidity information H at the center of the semiconductor substrates 200, and/or one or more humidity sensors configured to obtain a humidity information H at the edge of the semiconductor substrates 200. For example, in FIG. 6C, the apparatus 600 may have a humidity sensor 602 configured to obtain a humidity information H at the center of the semiconductor substrates 200, and a humidity sensor 604 configured to obtain a humidity information H at the edge of the semiconductor substrates 200. As with the embodiments in FIG. 5, the accuracy of the humidity factor ΔH may be increased, the rotation speed may be precisely controlled, and the fluctuation in the thickness of the resist layer formed on the semiconductor substrates 200 may be alleviated.

It should be noted that the apparatuses 500 and 600 in FIG. 5, FIG. 6A, and FIG. 6B may also being applied to the operation in FIG. 3A, FIG. 3B, FIG. 4A, and FIG. 4B. The description of the operation is similar and omitted herein for brevity.

Figure 7:
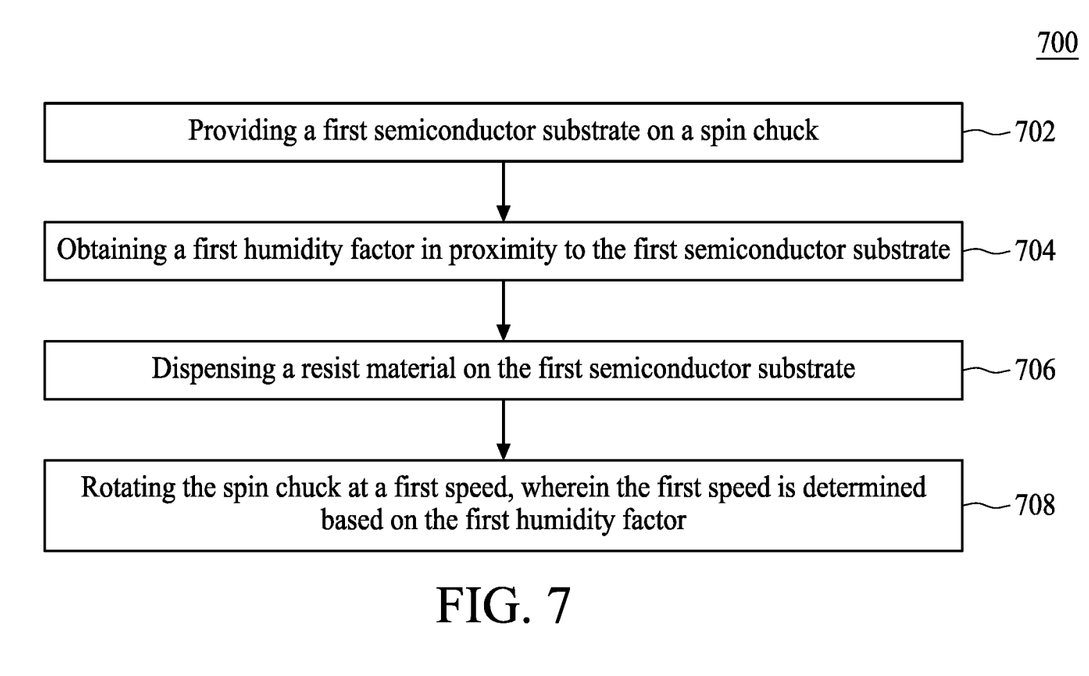
FIG. 7 is a flowchart showing a method for manufacturing a semiconductor structure, in accordance with some embodiments of the present disclosure.

FIG. 7 is a flowchart illustrating a method for manufacturing a semiconductor structure in accordance with some embodiments of the present disclosure. Referring to FIG. 7, in some embodiments, the method 700 includes operations 702, 704, 706 and 708. In operation 702, a first semiconductor substrate is provided on a spin chuck. In operation 704, a first humidity factor near the first semiconductor substrate is obtained. In operation 706, a resist material is dispensed on the first semiconductor substrate. In operation 708, the spin chuck is rotated at a first speed. The first speed is determined based on the first humidity factor. The operations are similar to the operations described in accordance with FIG. 1, FIG. 2, FIG. 3A, FIG. 3B, FIG. 4A, FIG. 4B, FIG. 5, FIG. 6A and FIG. 6B, and the detailed descriptions of such operations are omitted herein for brevity.

Figure 8:
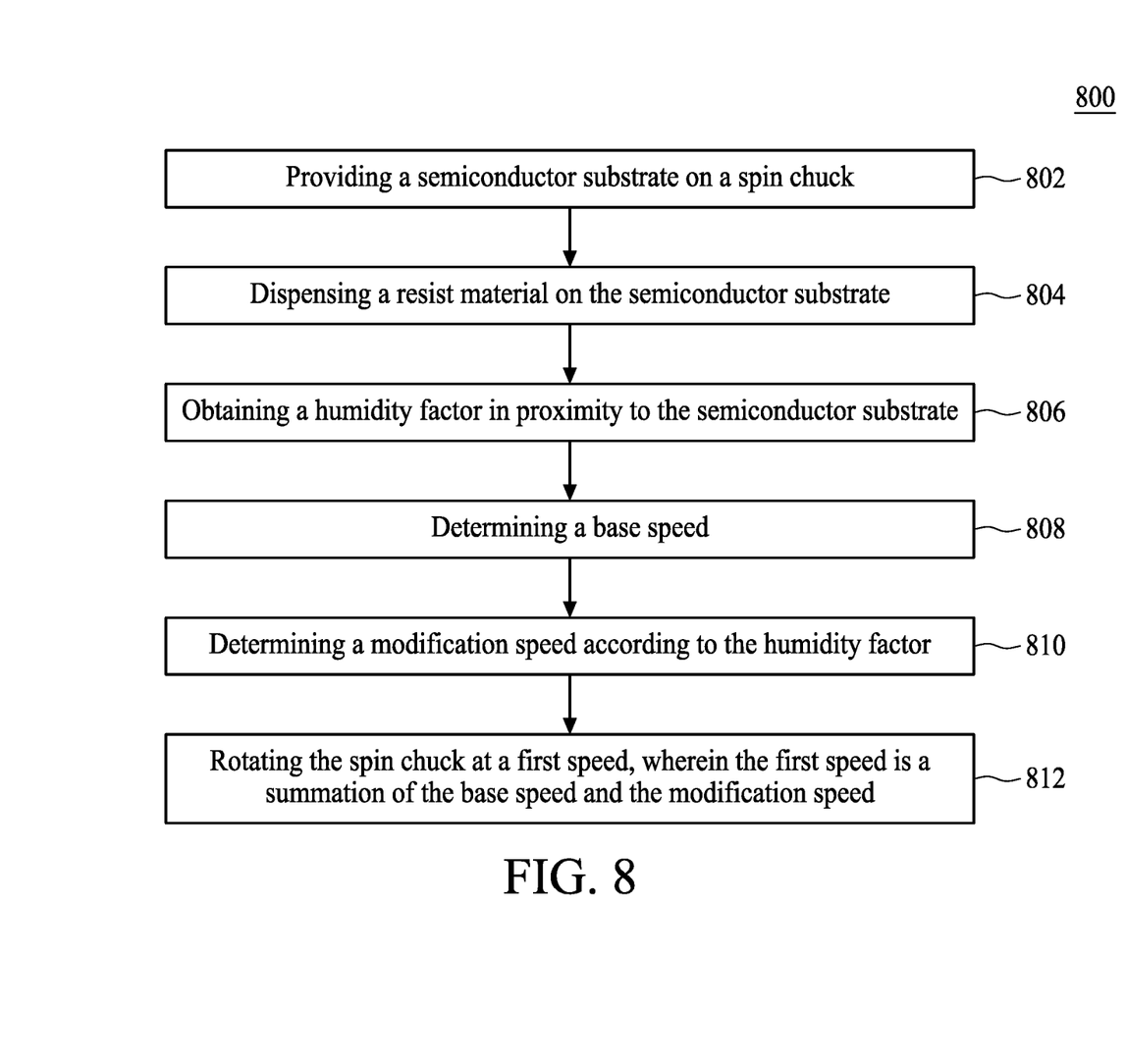
FIG. 8 is a flowchart showing a method for manufacturing a semiconductor structure, in accordance with some embodiments of the present disclosure.

FIG. 8 is a flowchart illustrating a method for manufacturing a semiconductor structure in accordance with some embodiments of the present disclosure. Referring to FIG. 8, in some embodiments, the method 800 includes operations 802, 804, 806, 808, 810 and 812. In operation 802, a semiconductor substrate is provided on a spin chuck.

In operation 804, a resist material is dispensed on the semiconductor substrate. In operation 806, a humidity factor near the semiconductor substrate is obtained. In operation 808, a base speed is determined. In operation 810, a modification speed according to the humidity factor is determined. In operation 812, the spin chuck is rotated at a first speed. The first speed is a summation of the base speed and the modification speed. The operations are similar to the operations described in accordance with FIG. 1, FIG. 2, FIG. 3A, FIG. 3B, FIG. 4A, FIG. 4B, FIG. 5, FIG. 6A and FIG. 6B, and the detailed descriptions of such operations are omitted herein for brevity.

In summary, the humidity level near the semiconductor substrate may affect the fluidity of the resist material. The thickness of the resist layer formed on the semiconductor substrate with the spin chuck rotating at the base speed may fluctuate because of the humidity variation. In some embodiments of the present disclosure, the rotation speed may be modified according to the humidity factor. Thus, the rotation speed may be increased or decreased according to the humidity level near the semiconductor substrate, and the fluctuation in the thickness of the resist layer formed on the semiconductor substrate may be alleviated.

According to some embodiments, a method for manufacturing a semiconductor structure is provided. The method includes the following operations. A first semiconductor substrate is provided on a spin chuck. A first humidity factor near the first semiconductor substrate is obtained. A resist material is dispensed on the first semiconductor substrate. The spin chuck is rotated at a first speed. The first speed is determined based on the first humidity factor.

According to other embodiments, a method for manufacturing a semiconductor structure is provided. The method includes the following operations. A semiconductor substrate is provided on a spin chuck. A resist material is dispensed on the semiconductor substrate. A humidity factor near the semiconductor substrate is obtained. A base speed is determined. A modification speed is determined according to the humidity factor. The spin chuck is rotated at a first speed. The first speed is a summation of the base speed and the modification speed.

According to other embodiments, an apparatus for manufacturing a semiconductor structure is provided. The apparatus includes a spin chuck, a dispensing unit and a humidity sensor. The spin chuck is configured to support a semiconductor substrate and rotate at a first speed. The dispensing unit is configured to dispense a resist material onto the semiconductor substrate. The humidity sensor is configured to sense a humidity information near the semiconductor substrate.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method for manufacturing a semiconductor structure, comprising:
   providing a first semiconductor substrate on a spin chuck;
   obtaining a first humidity factor near the first semiconductor substrate, comprising:
     sensing a plurality of humidity information; and
     determining the first humidity factor based on the plurality of humidity information;
   dispensing a first resist material on the first semiconductor substrate; and
   rotating the spin chuck at a first speed, wherein the first speed is determined based on the first humidity factor.

2. The method of claim 1, further comprising:
   removing the first semiconductor substrate from the spin chuck;
   providing a second semiconductor substrate on the spin chuck; and
   obtaining a second humidity factor near the second semiconductor substrate.

3. The method of claim 2, further comprising:
   reducing the first speed to a second speed when the second humidity factor is a negative value.

4. The method of claim 2, further comprising:
   increasing the first speed to a second speed when the second humidity factor is a positive value.

5. The method of claim 1, further comprising:
   obtaining a second humidity factor near the first semiconductor substrate;
   dispensing a second resist material on the first semiconductor substrate; and
   rotating the spin chuck at a second speed, wherein the second speed is determined based on the second humidity factor.

6. The method of claim 1, wherein the sensing of the plurality of humidity information is conducted by a plurality of sensors over the first semiconductor substrate.

7. The method of claim 1, wherein the determining the first humidity factor further comprises:
   obtaining an average data of the plurality of humidity information.

8. The method of claim 1, wherein the rotating of the spin chuck at a first speed according to the first humidity factor further comprises:
   rotating the spin chuck at a base speed; and
   changing the base speed to the first speed.

9. The method of claim 1, wherein the first speed is a summation of a base speed and a modification speed, wherein the modification speed is dependent on the first humidity factor.

10. The method of claim 1, further comprising:
    obtaining a material parameter of the resist material; and
    providing a base speed prior to determining the first speed.

11. The method of claim 8, further comprising:
    dispensing a second resist material on the first semiconductor substrate; and
    rotating the spin chuck for a rotating duration, wherein the rotating duration is determined based on a second humidity factor near the second semiconductor substrate.

12. A method for manufacturing a semiconductor structure, comprising:
    providing a semiconductor substrate on a spin chuck;
    dispensing a resist material on the semiconductor substrate;
    obtaining a humidity factor, comprising:
      sensing a first humidity information at a first position near the semiconductor substrate;
      sensing a second humidity information at a second position near the semiconductor substrate, wherein the second position is different from the first position; and
      determining the humidity factor according to the first humidity information and the second humidity information;
    determining a base speed;
    determining a modification speed according to the humidity factor; and
    rotating the spin chuck at a first speed, wherein the first speed is a summation of the base speed and the modification speed.

13. The method of claim 12, wherein the obtaining of the modification speed according to the humidity factor comprises:
    obtaining a material parameter of the resist material; and
    determining the modification speed according to the humidity factor and the material parameter.

14. The method of claim 13, further comprising determining the base speed according to the material parameter.

15. The method of claim 14, wherein the modification speed is dependent on the humidity factor.

16. A method for manufacturing a semiconductor structure, comprising:
    providing a semiconductor substrate on a spin chuck;
    dispensing photoresist over the semiconductor substrate;
    determining a base speed, wherein the base speed is dependent on a viscosity of the photoresist;

obtaining a first humidity factor over a center area of the semiconductor substrate;

obtaining a second humidity factor over a peripheral area of the semiconductor substrate;

determining a modification speed according to the first and second humidity factor; and rotating the spin chuck at a first speed, wherein the first speed is a summation of the base speed and the modification speed.

17. The method of claim 16, wherein the photoresist is dispensed over the semiconductor substrate prior to obtaining the first and second humidity factor.

18. The method of claim 16, wherein the photoresist is dispensed over the semiconductor substrate subsequent to obtaining the first and second humidity factor.

19. The method of claim 16, further comprising determining a duration of rotating the spin chuck at the first speed based on the first and the second humidity factor.

20. The method of claim 12, wherein the first humidity information is obtained by a sensor attached to a cup surrounding the spin chuck.

\* \* \* \* \*